United States Patent [19]

Ruhenstroth-Bauer et al.

[11] 4,341,765

[45] Jul. 27, 1982

[54] DRUG FOR ENHANCING LIVER GROWTH AND METHOD OF PREPARING SAME

[75] Inventors: Gerhard Ruhenstroth-Bauer, Gräfelfing; Michel Goldberg; Siegfried Silz, both of Munich; Wolfgang Strecker, Eichenau, all of Fed. Rep. of Germany

[73] Assignee: Max-Planck-Gesellschaft zur Foerderung der Wissenschaften E.V., Fed. Rep. of Germany

[21] Appl. No.: 130,648

[22] Filed: Mar. 17, 1980

Related U.S. Application Data

[63] Continuation of Ser. No. 28,304, Apr. 9, 1979, abandoned, which is a continuation-in-part of Ser. No. 973,666, Dec. 27, 1978, abandoned.

[30] Foreign Application Priority Data

Apr. 7, 1978 [DE] Fed. Rep. of Germany ....... 2814981

[51] Int. Cl.³ ............... A61K 35/14; A61K 37/00; A61K 35/407; C07G 7/00
[52] U.S. Cl. ............... 424/101; 260/112 R; 424/106; 424/177
[58] Field of Search ............... 424/101, 106, 177; 260/112 R

[56] References Cited

U.S. PATENT DOCUMENTS

| | | | |
|---|---|---|---|
| 2,045,266 | 6/1936 | Fenger | 260/112 R |
| 2,710,293 | 6/1955 | Gerlaugh | 260/112 B |
| 3,583,968 | 6/1971 | Pien | 260/112 R |
| 3,718,541 | 2/1973 | Kalina | 260/112 R |
| 3,876,774 | 4/1975 | Fortini et al. | 424/177 |
| 3,880,989 | 4/1975 | Garcia | 424/101 |
| 3,994,870 | 11/1976 | Newaith | 260/112 B |
| 4,024,247 | 5/1977 | Fortini et al. | 424/177 |
| 4,027,013 | 5/1977 | Bick et al. | 260/112 B |
| 4,054,557 | 10/1977 | Sievertsson et al. | 260/112 R |
| 4,057,628 | 11/1977 | Bick | 424/101 |

FOREIGN PATENT DOCUMENTS

| | | | |
|---|---|---|---|
| 2426584 | 9/1975 | Fed. Rep. of Germany | 424/106 |
| 7722M | 3/1970 | France | 424/106 |
| 565986 | 12/1944 | United Kingdom | 424/106 |

OTHER PUBLICATIONS

Bauer et al., Hoppe–Seyler's, Z. Physiolo. Chem. Bd., 359, S.543–545, (1978).

*Primary Examiner*—Douglas W. Robinson
*Attorney, Agent, or Firm*—Keil & Witherspoon

[57] ABSTRACT

A factor which causes an increase in the number of liver cells through increased cell division activity, obtained by homogenizing the remaining livers of partially hepatectomized animals, subjecting the homogenate to acidification to pH=5.5 and then heat treatment at 95° C., and centrifuging said homogenate. After such treatment, the factor is contained in the supernatant. The factor is a neuraminic-acid-free protein with a molecular weight of approximately 30,000 to 50,000 D. An extract containing the factor also can be obtained from the blood plasma of hepatectomized animals, when the plasma in addition to the described steps further is treated with neuraminidase. Similarly, an extract containing the factor can be obtained from the livers or the plasma of non-hepatectomized fetal or very young animals.

8 Claims, No Drawings

DRUG FOR ENHANCING LIVER GROWTH AND METHOD OF PREPARING SAME

This application is a co-pending continuation application of our application Ser. No. 28,304, filed Apr. 9, 1979, now abandoned, which in turn is a continuation-in-part of application Ser. No. 973,666, filed Dec. 27, 1978, and now abandoned.

The invention relates to a factor for stimulating the rate of proliferation of liver cells.

BACKGROUND OF THE INVENTION

It is known that liver growth is governed by two governing systems, of which one controls the growth of the volume of the liver cells and the other controls the increase in the number of liver cells (rate of proliferation). It is also known that when a portion of the liver is surgically removed (partial hepatectomy), a rate of proliferation of the liver cells much higher than normal, that is, a much greater level of cell division activity, occurs. This results in a great increase in the number of liver cells, which had been reduced by the operation, until the original number of liver cells has again been approximately attained. Such an increase in number of liver cells can also be observed in mammals in the fetal state or in the first weeks after birth. This increase takes place up to a certain number of cells. From that point, liver growth resumes by means of cell volume enlargement.

It has already been suspected that the control of the liver cell proliferation rate takes place by means of a liver cell proliferation factor or composition. However, equal consideration has been given to the possibility that there is a factor which under normal conditions inhibits cell division and, in the case of partial hepatectomy, disappears as the result of influences which are so far unknown. (See, as an example, the summary of knowledge in the field to that date in: Bucher, N. L. R. and Malt, R. A., *Regeneration of Liver and Kidney*, Boston: Little, Brown and Co., 1971, pp. 245 ff.)

OBJECT AND SUMMARY OF THE INVENTION

It is the object of the invention to obtain factors or compositions which cause an increase in number of the liver cells through increased cell division activity, that is, which cause a stimulation of the liver cell proliferation rate.

Therefore, it has been possible for the first time to provide, by a simple method, an active substance containing the liver cell proliferation factor (hereinafter called simply "factor") by means of extraction of the remaining livers of partially hepatectomized animals.

A preliminary factor containing the mentioned factor in a yet inactive form can be obtained by means of extraction from the blood plasma of partially hepatectomized animals or of non-hepatectomized foetal animals or non-hepatectomized animals in the first weeks after birth. It was possible to determine that the factor had was a protein or a substance containing protein and has a molecular weight of approximately 30,000 to 50,000 D. The extreme lower limit for molecular weight appears to be approximately 20,000 or 25,000 D. Thus, an extract containing this factor, can clearly be defined and manufactured. The methods of production of such materials in accordance with the invention, although extremely advantageous and simple, are solely given by way of example. It may be expected that after the disclosure of the liver cell proliferation factor in the form of the invention, further possibilities of production, including synthesis, will be rapidly developed or discovered.

There is a wide field of medical application for such a liver cell proliferation factor. In principle, by a drug containing such factor, all such diseases could be treated wherein the liver cells are in any way diseased and where the growth of new, healthy cells represents an appropriate therapy (such as hepatitis or cirrhosis of the liver). In this respect, it is of particular advantage that the substance found in accordance with the invention functions in an organ-specific manner (that is, only stimulates the growth of liver cells, not of kidney or spleen cells, for example), but not in a species-specific manner, so that substances obtained from partially hepatectomized livers of a certain species (rats) are also effective in other species, which can be demonstrated in mice.

The name "Hepatopoietin" is appropriate for this factor, in accordance with the conventional formulation of scientific nomenclature (cf. Erythropoietin).

DETAILED DESCRIPTION

A first means for concentrating the factor from the remaining livers of partially hepatectomized laboratory animals is described below:

The experiments were performed using female, specifically pathogen-free Wistar rats (obtained from the Institut für Strahlen- und Umweltforschung, Neuherberg/Munich) weighing between 95 and 105 grams. Before and after treatment, they were fed a diet of water and the preparation obtainable under the trade name "Altromin" in the desired amounts.

All the animals were subjected to a 68% partial hepatectomy, that is, a partial removal of the liver. In consideration of the daily course of liver cell proliferation activity in normal rats, the surgery was performed between 7 and 9 p.m. The partial hepatectomy was performed in accordance with the procedure of Higgins and Anderson (Arch. Path. (Chicago) 12, 186 (1931)).

In each case, the animals were sacrificed 12 hours after the partial hepatectomy. Under light anesthesia, the animals were bled and the remaining livers were removed; before removal, the livers were irrigated with a 0.9% saline solution through the portal vein. The remaining livers of three animals at a time were homogenized in the well-known Elvehjem-Potter homogenizer together with four times the quantity by weight (w/w) of twice-distilled water. The liver cells were thereby comminuted and, as completely as possible, destroyed. The liver cells placed in a glass cylinder were brought between the glass cylinder and a Teflon pin rotating therein and were opened or triturated by the resultant shear forces. In this manner, it was assured that substances contained in the cells were made available for the subsequent process of concentration or isolation.

These liver cell homogenates were brought to a pH level of 5.5 with a hydrochloric acid solution at a concentration of 0.1 N. This acidification is an important means of selection for eliminating a large number of proteins. In this manner, they are precipitated out and thus withdrawn from the further concentration or isolation process. Next, the liver homogenates were heat-denatured at a temperature of 95° C. for a period of 20 minutes. This is intended to further eliminate those components of the homogenate which are not stable at this temperature and at this pH level.

By means of these method steps, that is, the acidification to pH 5.5 and the heat-denaturation, a large proportion of the liver cell components is removed. Next, the homogenate is centrifuged for a period of 15 minutes with 4000 g (the apparatus used was a Minifuge Christ, Osterode/Harz, Germany). The supernatant, after centrifuging, thus contains only those active ingredients, out of all the ingredients contained in the original homogenate, which are stable at both a pH of 5.5 and a temperature of 95° C. However, it contains these in a purified form. Now in order to obtain also those portions of these active ingredients which may still be contained in the precipitates resulting from centrifuging, these precipitates were mixed with twice-distilled water to bring them up to the original volume again, subjected again to acidification to a pH of 5.5 and to heat-denaturation and finally centrifuged. Altogether, this was repeated twice.

The supernatants of these three centrifuging procedures were added and lyophilized, that is, subjected to freeze-drying by withdrawing water in a vacuum, so that they were then available for further use in a pulverized form. Until further use, they were stored at −20° C. This substance was the extract of the remaining livers of the partially hepatectomized laboratory animals (hereinafter called TL extract).

Control animals whose livers had not been partially hepatectomized were sacrificed at the same time as the animals having partially hepatectomized livers. In their case, the entire liver was removed, after irrigation with a 0.9% saline solution. A quantity of liver from the control animals which was equivalent to the quantity of remaining livers of the experimental animals was treated in the same manner as the remaining livers of the experimental animals; that is, it was first brought to a pH of 5.5, then heat-denatured at 95° C., and finally centrifuged, with the last method steps being repeated twice for the precipitates. The supernatants were also lyophilized, and these were the extracts from animals having normal livers (hereinafter, NL extract).

The supernatant from the treatment of the remaining livers of the experimental animals, that is, the TL extract, contains the new liver cell proliferation factor Hepatopoietin. This was demonstrated as follows:

The TL extract was dissolved in a 0.9% saline solution. A quantity of 2 ml of the solution was injected into normal rats intraperitoneally (i.p.). The control animals were injected with the same quantity of the NL extract obtained from normal animals which had not been partially hepatectomized. Further control animals were injected with a 0.9% saline solution i.p.

The measurement of liver cell proliferation after injection of the TL extract was then undertaken by measuring the synthesis of DNA. This may be done by measuring the quantity of radioactive substances specifically incorporated into the DNA, that is, of $^3$H-methylthymidin (special activity, 25 Ci/mmol; source: Radiochem. Center, Amersham).

The experimental animals and the control animals were injected with 50 $\mu$Ci of $^3$H-methylthymidin 19 hours after the injection of the TL and NL extracts respectively. One hour alter, the animals were sacrificed. The liver was removed and stored at −20° C.

Extraction of the liver DNA was then performed in accordance with the procedure of Weinbren, K. and Woodward, E. (*Br. J. Exp. Path.* 45, 442-449 (1964)). A portion of this extract was used for a measurement of radioactivity. To this end, 1.5 ml of the PCA (perchloracetic acid) solution was neutralized with 0.5 ml NaOH at a concentration of 1 N. The resultant solution was mixed in a scintillation tube with 5 ml Triton X100 and 10 ml toluol (0.6 PPO; PPO=1,5-diphenyloxazole). With the aid of a liquid scintillation counter (source: Intertechnique, Paris), the radioactivity was then determined as the number of disintegrations per minute. A further portion of the DNA extract was used for measurement of the DNA concentration in accordance with Burton (Biochem. J. 62, 315-323 (1956)). Thus, as a standard for DNA synthesis, one obtains the specific activity in disintegrations per minute per microgram of DNA per gram of liver.

On the average, the normal rats injected with NL extract showed, under the experimental conditions cited, an average specific activity of 3340±1320 disintegrations per minute per microgram of DNA per gram of liver (number of experimental animals: n=8). In the normal rats injected with a physiological saline solution, a value of 3470±740 (n=8) was obtained. Thus the activity in both groups of animals was substantially identical.

In the case of the animals injected with TL extract, in contrast, a very much greater activity was ascertained, namely an average specific activity of 11,240±4730. In comparison with the controls (NL extract and NaCl), this produces an increase by the factor of 3.3 and with great statistical accuracy (p< <0.01). Thus, it is demonstrated that the i.p. injection of the extract derived in the manner described from partially hepatectomized livers causes a great increase in DNA synthesis in normal animals, which synthesis in turn is a necessary precondition for cell division and thus for liver growth through cell division.

In order to ascertain whether the increase in DNA synthesis which had taken place also led in fact to a corresponding actual increase in the number of liver cells, the rate of proliferation of liver cells was measured at the same time; that is, a mitosis count was performed. To this end, 24 hours after the injection of NL or TL extract, the rats were bled and the livers removed; before removal, the livers were irrigated through the portal vein with a 0.9% saline solution. The histological preparation was performed in accordance with Pera (Histochem. 30, 82 (1972)) and Silz et al. (*Acta Hepagastroenterol.* 23, 255-261 (1976)). To this end, a portion of the caudate lobe was used. Sections 5 $\mu$m in thickness were taken and stained with hematoxylineosin. The rate of mitosis was determined by counting out 10,000 cells per section.

Counting the rate of mitosis showed that the injection of TL extract had also caused an actual increase in the rate of proliferation of the liver cells. The mitosis index, determined twice, amounted to 7 and 4 mitoses respectively per $10^4$ cells, compared with between 0 and 2 mitoses per $10^4$ cells in normal rats.

This result confirms that the extract of partially hepatectomized liver cells, obtained in the above-described manner contains a factor, which stimulates the proliferation of liver cells and, when injected i.p. into normal rats causes a genuine increase of the rate of proliferation of liver cells.

In order to determine qualitatively the factor contained in the TL extract, the following experiments were carried out:

(a) Enzymatic Treatment (aa) A trypsin-chymotrypsin treatment was performed. To this end, the lyophilized supernatants were dissolved in 20 ml of twice-distilled water, brought to pH 7.6 and incubated at 30° C. for a period of 2 hours with 80 U of trypsin, purest grade, and 90 U of α-chymotrypsin, purest grade (source: Serva, Heidelberg). Next, it was incubated for a period of 30 minutes at 95° C. and subsequently centrifuged. The solution was lyophilized. Experimental animals (rats) were injected i.p. with 2 ml of a 0.9% saline solution. Typically, this procedure, when performed with proteins or proteides, causes their hydrolysis and thus their inactivation.

This was the result in this case as well. The enzymatic incubation caused the destruction of the activity. A radioactivity of 3234±1340 (n=5) resulted. From this, it may be inferred that the factor is a protein or a proteide.

(bb) In addition, a *neuraminidase* treatment was carried out. To this end, the lyophilized supernatants were each dissolved in 20 ml of twice-distilled water, brought to pH 5.5, and incubated for one hour at 37° C. with 250 U neuraminidase preparation (source: Behring-Werke, Marburg). Next, the excess neuraminidase was inactivated at 95° C. during a period of 30 minutes, centrifuged (15 minutes, 3000×g) and again lyophilized. The lyophilized product was dissolved in 2 ml of 0.9% saline solution and injected i.p. into the experimental animals (rats). An enzymatic treatment of this sort, when performed on glycoproteins containing neuraminic acid, typically causes a splitting off of the neuraminic acid and thus causes inactivation.

In the present case, an inactivation of this sort did not occur. On the contrary, the incorporation activity of the $^3$H-methylthymidin in DNA and the radioactivity of the extracted DNA created thereby remained very high. The resultant value was 13,900±5650 (n=3). From this, it may be inferred that the factor obtained in the manner described above by means of extraction from partially hepatectomized livers is not a substance containing a neuraminic acid of significance for this activity.

(b) Determination of the Molecular Weight

To this end, the TL extract was pressure-filtered through a molecular filter (source: Amicon, Lexington, U.S.A.) of various pore sizes. Upon filtration through the PM 30 filter, the entire activity was retained. The specific activity of the extract after pressure-filtration through a PM 30 filter demonstrated a concentration approximately 100 times greater than in the unfiltered material. The molecular weight accordingly lies above approximately 30,000 Dalton (D). Upon pressure-filtration through the XM 50 filter, approximately half the activities remain in the filtrate, while the other half was retained in the filter. This indicates that the molecular weight lies approximately between 30,000 and 50,000 D. While the upper limit of the range may be stated with relatively great assurance to be 50,000 D, the lower limit is only an approximate value. Molecular weights of 20,000 or 25,000 D may possibly also be involved.

The activity of the discovered factor is at least in part organ-specific. Radioactive incorporation into spleen or kidney tissue when TL extract was injected was not distinguishable from that when NL or NaCl was injected as a control.

On the other hand, it was demonstrated that the factor is not species-specific. An injection of the TL extract into NMRI mice (21–24 grams, specifically pathogen-free, source: Institut für Strahlen- und Umweltforschung, Neuherberg/Munich) caused the same result as in rats (TL: 12,050±6510; NL: 4350±530; NaCl: 3240±1810; n=5).

A second means of obtaining the activating factor for liver cell proliferation is described below:

The point of departure was the following consideration: In the described experiments, the injection was made into the abdominal cavity (i.p.). Thus, the TL extract must be transported into the liver through the circulatory system. It may therefore also be present in the circulatory system. Therefore, the blood plasma was removed, under the same experimental conditions, from rats whose livers had been partially hepatectomized in the same manner as that described above, and an extract was produced in the same manner as is described above pertaining to the remaining livers.

When this blood plasma extract from animals having partially hepatectomized livers (PT) is injected into normal rats, there is no indication of liver cell proliferation rate stimulation (3800±960; n=5). However, if such a PT extract is treated with neuraminidase, then a highly proliferation-stimulating substance results 15380±4730; n=4). Thus, a further means of obtaining the factor is disclosed. A corresponding extract made from normal plasma causes no increase after neuraminidase treatment.

If the preliminary factor thus obtained from the blood plasma is incubated with a trypsin-chymotrypsin mixture, as has just been described for the extract of partially hepatectomized livers, then here, as well, the liver cell proliferation activity is destroyed. This proves that the active factor in PT is also a protein or proteide. The factors derived from liver and from plasma are thus related to one another.

From the above, the following can be inferred concerning the mechanism of the function: The factor in TL itself contains no neuraminic acid. The preliminary factor as present in the circulatory system, in contrast, is a neuraminic acid-containing protein. In this form, it is still-inactive. The neuraminic acid is split off by means of neuraminidase. An active factor is the result. Now, it is already known that after a partial hepatectomy a spontaneous concentration of neuraminidase takes place in the liver itself. It is probable that this releases the active factor from the preliminary factor. This also explains why the injection of PT extract, that is, the still-inactive preliminary form itself, does not yet result in an increase in liver cell proliferation rate in normal rats. In normal, not partially hepatectomized livers, the neuraminidase required for transforming the preliminary form into the active principle is not present, or is insufficiently present to cause the splitting off of the neuraminic acids and thus the final preparation of an active factor. This occurs only through the neuraminidase, which is present in increased amounts in partially hepatectomized livers.

However, it is also possible that the transformation of the still-inactive preliminary factor into the active factor takes place as a result of neuraminyltransferase. This could occur equally well in the blood plasma or in the liver cells themselves. However, it is more likely that it takes place in the blood plasma itself, since the preliminary factor, after treatment with neuraminidase, is of course injected intraperitoneally and from there reaches the liver cells by way of the blood. Accordingly, there must be receptors in the liver cells which bind the neuraminic acid-free form. This implies that the preliminary factor is already transformed into the neuraminic acid-free form in the blood.

On the other hand, in partially hepatectomized liver cells, the neuraminidase concentration in the liver increases sharply. This enzyme, which can be found there, could therefore also be responsible for the transformation of the preliminary factor (inactive and containing neuraminic acid) into the neuraminic acid-free and active form.

A third and fourth means for obtaining the liver cell proliferation-stimulative factor are provided by extracting the (complete, not partially hepatectomized) livers and blood plasma, respectively, of fetal mammals or of mammals in the first few weeks after birth in the manner described, since, as was mentioned at the outset, it is known that up to such an age, the cell proliferation rate is very much higher than in older animals, even in the case of normal (that is, not partially hepatectomized) animals. In this event as well, the extraction of the blood plasma at first provides the still-inactive preliminary factor, which can be activated by the action of neuraminidase.

The extraction procedures described cause an isolation or concentration of the factor contained in the liver cells. Thus, in principle, it is already contained in the liver homogenate which has not yet been extracted. However, its presence can not be demonstrated in whole-liver extract, because such whole-liver extracts are extremely toxic and animals injected with them die.

The time values given, for instance for the period between partial hepatectomy and the sacrifice of the experimental animals, between injection of the extracts and injection of the thymidin, etc., are values which have proved to be particularly favorable in terms of the yield and replicability. The value given for temperature of denaturing is an upper limit. The factor or preliminary factor in accordance with the invention is simultaneously stable at the cited values for pH and temperature.

What is claimed is:

1. A factor for stimulating the rate of proliferation of liver cells isolated by a process comprising the steps of, providing remaining livers from partially hepatectomized animals, homogenizing said remaining livers to provide a liver homogenate, acidifying said liver homogenate to a pH value of approximately 5.5, heat denaturing said acidified liver homogenate to a temperature of approximately 95° Centigrade, subsequently centrifuging said liver homogenate to provide a supernatant containing said factor, said factor exhibiting the characteristics of a neuraminic acid-free protein or proteide having a molecular weight of approximately 30,000 to 50,000 D which is stable at a pH level of 5.5 or greater and at a temperature of 95° Centigrade or lower.

2. A factor for stimulating the rate of proliferation of liver cells isolated by a process comprising the steps of, providing the blood plasma of animals having partially hepatectomized livers, acidifying said blood plasma to a pH value of approximately 5.5, heat denaturing said acidified blood plasma homogenate to a temperature of approximately 95° Centigrade, subsequently centrifuging said blood plasma and treating the supernatant with neuraminidase to obtain said factor, said factor exhibiting the characteristics of a neuraminic acid-free protein or proteide having a molecular weight of approximately 30,000 to 50,000 D which is stable at a pH level of 5.5 or greater and at a temperature of 95° Centigrade or lower.

3. A factor for stimulating the rate of proliferation of liver cells isolated from livers of foetal animals or animals of the age of a few weeks by a process comprising homogenizing said livers to provide a liver homogenate, acidifying said liver homogenate to a pH value of approximately 5.5, heat denaturing said acidified liver homogenate to a temperature of approximately 95° Centigrade, subsequently centrifuging said liver homogenate to provide a supernatant containing the factor, said factor exhibiting the characteristics of a neuraminic acid-free protein or proteide having a molecular weight of approximately 30,000 to 50,000 D which is stable at a pH level of 5.5 or greater and at a temperature of 95° Centigrade or lower.

4. A factor for stimulating the rate of proliferation of liver cells isolated by a process comprising the steps of, providing the blood plasma from foetal animals or from animals of the age of just a few weeks, acidifying said blood plasma to a pH value of approximately 5.5, heat denaturing said acidified blood plasma to a temperature of approximately 95° Centigrade, subsequently centrifuging said blood plasma and treating the supernatant with neuraminidase to obtain said factor, said factor exhibiting the characteristics of a neuraminic acidfree protein or proteide having a molecular weight of approximately 30,000 to 50,000 D which is stable at a pH level of 5.5 or greater and at a temperature of 95° Centigrade or lower.

5. A pharmaceutical composition containing the factor of claim 1 in a therapeutically effective amount and a pharmaceutically acceptable carrier therefor.

6. A pharmaceutical composition containing the factor of claim 2 in a therapeutically effective amount and a pharmaceutically acceptable carrier therefor.

7. A pharmaceutical composition containing the factor of claim 3 in a therapeutically effective amount and a pharmaceutically acceptable carrier therefor.

8. A pharmaceutical composition containing the factor of claim 4 in a therapeutically effective amount and a pharmaceutically acceptable carrier therefor.

* * * * *

UNITED STATES PATENT AND TRADEMARK OFFICE
CERTIFICATE OF CORRECTION

PATENT NO. : 4,341,765
DATED : July 27, 1982
INVENTOR(S) : Gerhard Ruhenstroth-Bauer, Michel Goldberg,
Siegfried Silz and Wolfgang Strecker It is certified that error appears in the above—identified patent and that said Letters Patent is hereby corrected as shown below:

On the patent information page, under "Related U.S. Application Data delete "continuation-in-part" and insert --continuation--.

In Column 1, line 7, delete the hyphen after the word "continuation";

line 8, delete "in-part" at the beginning of the line.

In Column 3, line 64, "alter" should read --later--.

Signed and Sealed this

Twenty-first Day of December 1982

[SEAL]

Attest:

GERALD J. MOSSINGHOFF

Attesting Officer

Commissioner of Patents and Trademarks